US012029455B2

(12) United States Patent
Gokcen et al.

(10) Patent No.: US 12,029,455 B2
(45) Date of Patent: Jul. 9, 2024

(54) ANKLE ARTHRODESIS USING RETROGRADE HINDFOOT NAIL

(71) Applicant: McGinley Engineered Solutions, LLC, Casper, WY (US)

(72) Inventors: Eric Cemil Gokcen, Langhorne, PA (US); Joseph C. McGinley, Casper, WY (US); Alice Pinter, Casper, WY (US); Adam Johnson, Casper, WY (US); Vincent Palazzolo, Casper, WY (US)

(73) Assignee: MCGINLEY ENGINEERED SOLUTIONS, LLC, Casper, WY (US)

( * ) Notice: Subject to any disclaimer, the term of this patent is extended or adjusted under 35 U.S.C. 154(b) by 0 days.

(21) Appl. No.: 18/189,875

(22) Filed: Mar. 24, 2023

(65) Prior Publication Data
US 2023/0301692 A1 Sep. 28, 2023

Related U.S. Application Data

(60) Provisional application No. 63/323,234, filed on Mar. 24, 2022.

(51) Int. Cl.
A61B 17/72 (2006.01)
A61B 17/80 (2006.01)

(52) U.S. Cl.
CPC ........ A61B 17/7225 (2013.01); A61B 17/725 (2013.01); A61B 17/7291 (2013.01); A61B 17/808 (2013.01)

(58) Field of Classification Search
CPC ............ A61B 17/7095; A61B 17/7225; A61B 17/725; A61B 17/7291; A61B 17/808
See application file for complete search history.

(56) References Cited

U.S. PATENT DOCUMENTS

RE46,008 E     5/2016  Janna et al.
2002/0055744 A1*  5/2002  Reiley ................ A61B 17/1775
                                                        623/21.18

(Continued)

OTHER PUBLICATIONS

International Search Report and Written Opinion completed for Application PCT/US2023/016301 by the U.S. Commissioner of Patents on May 24, 2023.

Primary Examiner — Ariana Zimbouski
Assistant Examiner — Christine L Nelson
(74) Attorney, Agent, or Firm — HOLZER PATEL DRENNAN

(57) ABSTRACT

An intermedullary nail for targeted arthrodesis of the tibiotalar joint. The intramedullary nail may be advanced through a bore extending through the calcaneus, talus, and into the tibia. In an example, a distal end portion of the intramedullary nail is disposed proximal to the subtalar joint. It has been recognized that creation of a bore for introduction of the intramedullary nail does not significantly disrupt the articular surface area of the subtalar joint. Furthermore, locking fasteners used to secure the intramedullary nail may introduced laterally and/or anteriorly to facilitate benefits in relation to patient placement and manipulation during an operation. Furthermore, arthrodesis may be extended to adjacent anatomy through use of extension plates at least partially secured by locking fasteners also engaging the intramedullary nail.

20 Claims, 18 Drawing Sheets

(56) References Cited

U.S. PATENT DOCUMENTS

| | | |
|---|---|---|
| 2003/0097131 A1 | 5/2003 | Schon et al. |
| 2006/0200141 A1 | 9/2006 | Janna et al. |
| 2011/0166608 A1 | 7/2011 | Duggal et al. |
| 2018/0085151 A1* | 3/2018 | Abdelgawad .......... A61B 17/72 |
| 2019/0365435 A1 | 12/2019 | Hintermann et al. |
| 2021/0038269 A1* | 2/2021 | Kearns ............... A61B 17/1725 |

* cited by examiner

ANKLE ARTHRODESIS USING RETROGRADE HINDFOOT NAIL

CROSS REFERENCE TO RELATED APPLICATIONS

The present application claims priority to U.S. Provisional Patent Application No. 63/323,234 filed on Mar. 24, 2022 entitled "ANKLE ARTHRODESIS USING RETROGRADE HINDFOOT NAIL," the entirety of which is incorporated by reference herein.

BACKGROUND

Ankle arthrodesis can be a challenging procedure requiring careful wound management, detailed preparation of the fusion site, and placement of stable rigid fixation. Current techniques of ankle arthrodesis include placement of either percutaneous cannulated screws or plate fixation. Percutaneous screw fixation provides improved wound management by utilizing small incisions for insertion of the screws. However, the benefit of smaller wounds is provided at the expense of maximizing fixation. Plate fixation significantly improves stability of the fused joint but requires a larger incision for implantation. In turn, the larger wound increases the risk of wound complications.

SUMMARY

The present disclosure generally relates to tibiotalar arthrodesis, which includes creating a bore extending from a plantar surface of a calcaneus bone through the calcaneus bone, subtalar joint, talus bone, and tibiotalar joint and terminating in intramedullary space of a tibia bone of a patient. In addition, the arthrodesis includes advancing an intramedullary nail through the bore and disposing a distal end portion of the intramedullary nail proximal to the subtalar joint. In turn, the intramedullary nail is secured with at least one tibia locking fastener and at least one talus locking fastener, each of which passes though respective apertures of the intramedullary nail. As such, the tibiotalar joint is compressed by applying a compressive force between the tibia locking fastener and the talus locking fastener, wherein the subtalar joint remains free to articulate.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein

DETAILED DESCRIPTION

Figure 1:
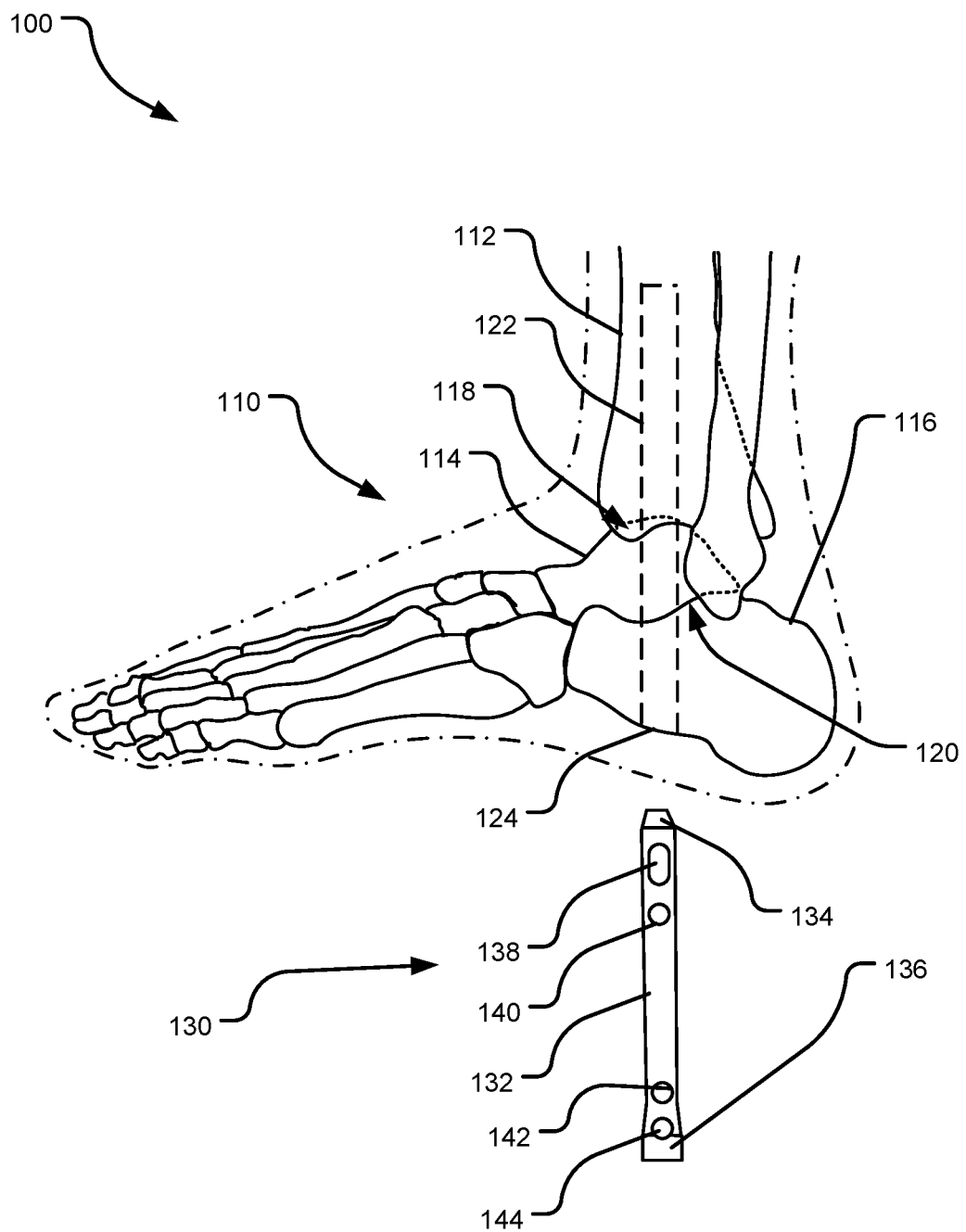
FIG. 1 includes a side view of an example of an intramedullary nail of the present disclosure in a retracted position.

Intramedullary fixation using an intramedullary nail for ankle arthrodesis may provide an optimal fixation method because use of the intramedullary nail may provide rigid, stable fixation beyond that achievable using a plate affixed externally to the ankle joint. The intramedullary nail may also be implantable using small incisions away from the fusion site, thus decreasing the risk of wound complications. As such, the respective benefits of percutaneous screws and plate fixation may both be facilitated using the intramedullary nail of the present disclosure.

Specifically, no intramedullary fixation devices have been developed for targeted arthrodesis of the tibiotalar joint. Concerns regarding entry access for the nail insertion have mostly precluded such development. Curved nail designs have been proposed for implantation through the sinus tarsi. However, insertion is quite difficult due to the need to create significant varus to insert the nail. In addition, no intramedullary nail has been developed for insertion through the calcaneus and subtalar joint for isolated arthrodesis of the tibiotalar joint. Rather, techniques used for insertion of intramedullary nails for tibiotalocalcaneal (TTC) arthrodesis have not been contemplated for use in targeted tibiotalar arthrodesis because it was assumed that such a use would significantly damage the subtalar joint.

However, the present disclosure recognizes that retrograde ankle nailing using an intramedullary nail can be performed to achieve isolated arthrodesis of the tibiotalar joint with negligible effects on the subtalar joint. The retrograde ankle nailing using the intramedullary nail may include linear advancement of the nail through the subtalar joint for placement relative to the tibiotalar joint. For instance, it has been found that creating a bore that extends through the subtalar joint for isolated arthrodesis of the tibiotalar joint results in only about 6% of the talar posterior facet and 4% of posterior facet of the calcaneus being damaged. In addition, it has been found that there is no damage to the middle facet in this approach.

Accordingly, it is presently recognized that use of a reamer or the like to create a bore across the subtalar joint for selective placement of an intramedullary nail across the tibiotalar joint resulted in removal of only about 3.4% of the calcaneal articular surface and only about 5.0% of the talar articular surface of the subtalar joint. As can be appreciated, drilling across foot joints for temporary fixation is done extensively, such as in the midfoot for LisFranc dislocation fixation. As such, the minimal levels of disruption to the subtalar joint may facilitate creation of a bore for selective placement of an intramedullary nail across the tibiotalar joint to achieve isolated arthrodesis of the tibiotalar joint with minimal disruption to the subtalar joint. Thus, use of the intramedullary nail for isolated tibiotalar arthrodesis may be achieved for improved joint stability and with reduced complications associated with wound care.

In view of the foregoing, the present disclosure generally relates to use of an intramedullary nail for isolated fixation of the tibiotalar joint using an arthroscopic approach for targeted ankle arthrodesis. Arthroscopic ankle arthrodesis has been shown extensively to provide faster and more reliable rates of fusion, in addition to less surgical pain and the ability to perform the surgery as an outpatient procedure. While the fixation for the arthroscopic approach has traditionally used percutaneous cannulated screws with external compression, this does not provide the optimal level of stable, rigid fixation. Moreover, plate fixation, while providing improved stability, requires a large incision which would defeat the purpose of performing the procedure arthroscopically. Accordingly, use of an intramedullary nail provides an improved solution for obtaining rigid fixation with an arthroscopic procedure. The resulting arthrodesis using the intramedullary nail is significantly more stable and rigid than percutaneous screws, it provides axial loading of the fusion site if dynamized, and it is implanted percutaneously through small incisions located away from the fusion site.

In some examples, an intramedullary nail as presented herein may be used for either TTC or isolated ankle arthrodesis (e.g., of the tibiotalar joint exclusively), and can be expanded to a pantalar arthrodesis using coordinating hardware as described herein. In this regard, arthrodesis of the talonavicular and/or calcaneocuboid joints may also be achieved.

In addition, the present disclosure may increase the ease and simplicity of implantation for the surgeon by inserting all locking fasteners used with the intramedullary nail from either anterior and/or lateral percutaneous approaches. In contrast, all current intramedullary nail designs require posterior fastener placement in the calcaneus. The posterior placement of the fastener may require the surgeon to have an assistant elevate and hold the leg for drilling, measurement, and fastener placement. As a result, guide sleeves used in placement of the fastener frequently are mishandled and may fall outside of the sterile field, which leads to delays in surgery while the guides and/or fasteners are resterilized. Similar issues are found with talar fasteners that are placed from a posterolateral position.

Other proposed options may include use a lateral approach which requires resection of the fibula, which presents additional complications. Placing the patient in a prone position is another option, but this orientation is not a familiar approach for most surgeons and requires significantly more set up time in the operating room. Proximal fasteners in current designs may also be placed from a medial approach which can be more difficult with the contralateral leg interfering with the instruments when placing the fasteners.

In contrast, the present disclosure may utilize anterior talar fastener placement and lateral calcaneal fixation using a fastener. This may avoid the foregoing disadvantages and difficulties of fastener placement by allowing the operative leg to remain in the supine position with no assistance needed to elevate it, while providing a familiar approach to the anatomy. In addition, use of lateral fastener placement may avoid any interference from the contralateral leg. In turn, not only does the present disclosure provide easier implantation for general use of the intramedullary nail, but also improves the ability to implant the nail for arthroscopic ankle fusions. The patient may remain in a supine position for both the arthroscopic preparation of the tibiotalar joint and for implantation of the intramedullary nail device. The foot may also be kept in the arthroscopy skin traction setup, but with the traction released, allowing for the surgeon to do the procedure without the need for any skilled surgical assistants or repositioning of the patient.

Further still, while isolated tibiotalar arthrodesis may be achieved using the intramedullary nail described herein, it may be determined further immobilization of the subtalar joint is desired after initial insertion of the intramedullary nail. In this regard, the intramedullary nail may be fitted with a tibiotalocalcaneal arthrodesis extension. The tibiotalocalcaneal arthrodesis extension may be engaged with the existing intramedullary nail such that tibiotalocalcaneal arthrodesis may be achieved using the same bore and approach as that initially used to place the intramedullary nail for tibiotalar arthrodesis. Accordingly, in the event a revision is desired to expand the arthrodesis to the subtalar joint, an initially placed intramedullary nail may be extended without requiring new or additional placement of hardware in the tibia and talus of the patient.

To facilitate an isolated tibiotalar arthrodesis, a jig may be utilized that allows for deeper insertion of an intramedullary nail for placement of the intramedullary nail in the talus to allow for isolated tibiotalar arthrodesis. The jig may include features that improve dynamic compression of the joint. For example, many current nail designs provide varying degrees of stability. The present disclosure may facilitate an increase in stability over proposed nail designs by locking the locking fasteners with respect to the intramedullary nail. This may provide a fixed angle at the fastener-nail interface. The locking of the fastener with respect to the nail may be accomplished by providing an inner cannula of the nail in communication with a channel of the jig. A set screw may be advanced through the plantar aspect of the channel of jig and through the inner cannula until it engages the locking screw. Such advancement may be facilitated by a threaded interface between the internal cannula and the set screw. This process to lock a fastener with respect to the nail may be repeated for each of the distal locking fasteners, beginning with insertion of a talus fastener, and proceeding to one or more additional distal fasteners.

Further still, no current hindfoot nail designs include any provisions for extending arthrodesis to a pantalar fusion by including the talonavicular and/or calcaneocuboid joints. The present disclosure contemplates hardware for selective fixation of the talonavicular and calcaneocuboid joints relative to the intramedullary nail. For instance, such extended arthrodesis may be provided by fixing a standard midfoot plate to the nail and locking it with an internal set screw.

Turning to the figures, FIG. 1 illustrates an example of an environment 100 in which an intramedullary nail 130 may be utilized for isolated arthrodesis of the tibiotalar joint 118. As illustrated in FIG. 1, anatomy of a patient 110 is illustrated including a distal portion of a tibia 112, a talus 114, and a calcaneus 116. The tibiotalar joint 118 is defined between the tibia 112 and the talus 114. In addition, the subtalar joint 120 is defined between the talus 114 and the calcaneus 116.

The tibiotalar joint 118 may be prepped for arthrodesis by using an arthroscopic approach for joint preparation. Furthermore, a bore 122 may be created that extends proximally from a plantar aspect 124 of the calcaneus 116. Specifically, the bore 122 may extend proximally into the tibia 112 such that the bore 122 may terminate in an intramedullary space of the tibia 112. That is, the bore 122 may extend from the plantar aspect 124 through the calcaneus 116, subtalar joint 120, talus 114, tibiotalar joint 118, and into the intramedullary space of the tibia 112. The bore 122 may be created by initially positioning a guide wire in a predetermined orientation relative to the anatomy of the patient 110. For example, the guide wire may be introduced, and the guide wire positioning may be confirmed via radiographs. In turn, a reamer or series of reamers may be utilized in conjunction with the guide wire to create a bore 122 with a diameter corresponding to the size of intramedullary nail 130.

The intramedullary nail 130 is shown in FIG. 1 in a retracted position. The intramedullary nail 130 may include a nail body 132 that extends between a proximal end portion 134 and a distal end portion 136. The nail body 132 may include a first proximal aperture 138 and a second proximal aperture 140. The proximal apertures 138 and 140 may be adapted to receive locking fasteners inserted through the tibia 112 as will be discussed in greater detail below. In an example, one or more of the first proximal aperture 138 or the second proximal aperture 140 may be elongated in an axial direction along the intramedullary nail 130. Furthermore, the distal end portion 136 may include a first distal aperture 142 and a second distal aperture 144 adapted to receive one or more locking fasteners introduced through the talus 114, which is also described in greater detail below. In this regard, upon application of a compressive force to a locking fastener disposed in a distal aperture, the elongated proximal aperture may allow for application of a compressive force across one or more joints that the intramedullary nail 130 passes.

The intramedullary nail 130 may be sized appropriately for targeted arthrodesis of the tibiotalar joint 118 such that the distal end portion 136 of the intramedullary nail 130 is located proximally to the subtalar joint 120 when positioned. In specific examples, the nail may be 10.0 mm in diameter. Furthermore, the locking fasteners may be 5.0 mm in diameter. The intramedullary nail 130 may have a length of 200 mm. The proximal apertures may be positioned approximately 100 mm and 120 mm, respectively, from the distal end portion 136. Other examples may also be provided such as an intramedullary nail 130 having a 11.5 mm diameter, and lengths of between about 150 mm and 300 mm. For example, the intramedullary nail 130 may have a length of 150 mm, 180 mm, 200 mm, 210 mm, 240 mm, 250 mm, 270 mm, or 300 mm.

Figure 2:
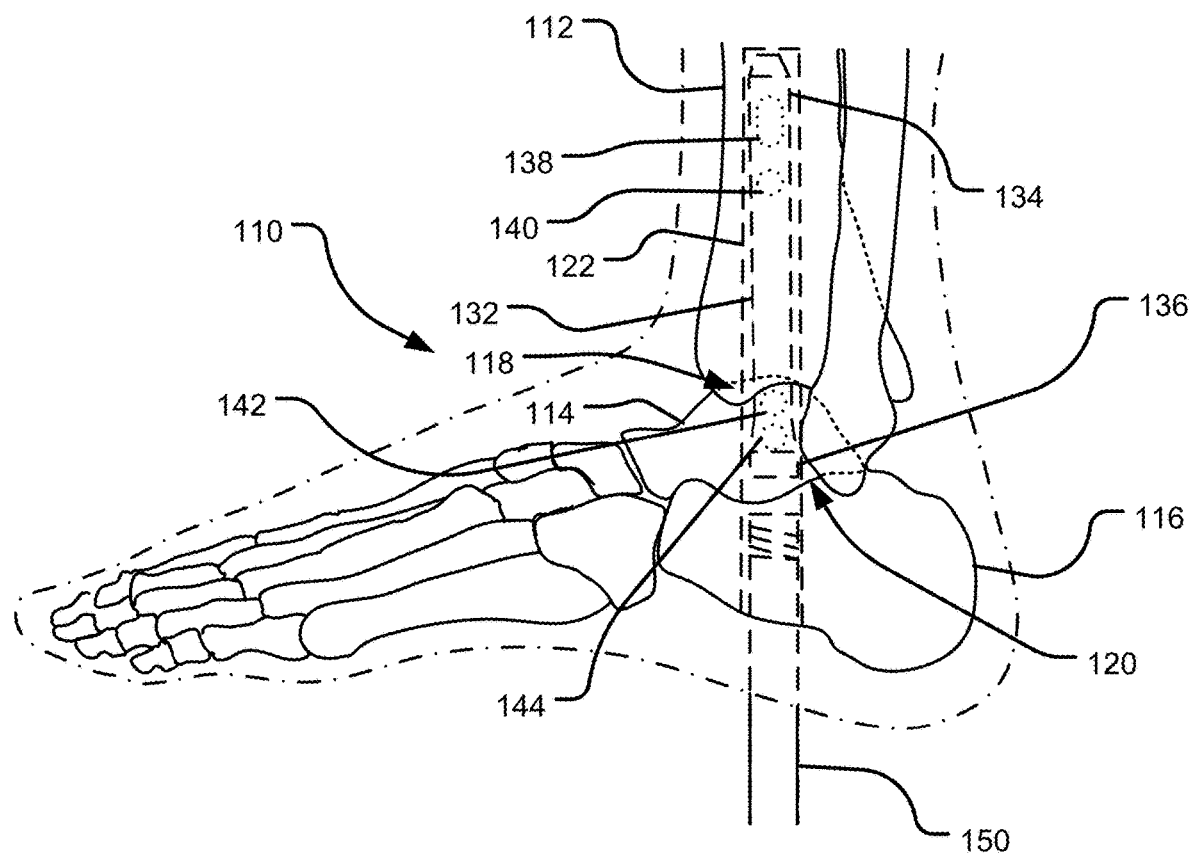
FIG. 2 includes a side view of an example of an intramedullary nail of the present disclosure in an inserted position.

With further reference to FIG. 2, the intramedullary nail 130 is shown in an inserted position relative to the tibia 112 and talus 114 for arthrodesis of the tibiotalar joint 118. Specifically, a fixture or fixture 150 may be engaged with the distal end portion 136 of the intramedullary nail 130. In turn, the fixture 150 may be utilized to advance the intramedullary nail 130 proximally through the bore 122 such that the intramedullary nail 130 passes through the calcaneus 116 and subtalar joint 120. In turn, the intramedullary nail 130 may be positioned such that the nail body 132 extends through the talus 114, tibiotalar joint 118, and into an intramedullary space of the tibia 112. That is, the distal end portion 136 of the intramedullary nail 130 may be positioned proximal to the subtalar joint 120. The subtalar joint 120 may be unaffected by the intramedullary nail with the exception of the creatin of bore 122.

Figure 14:
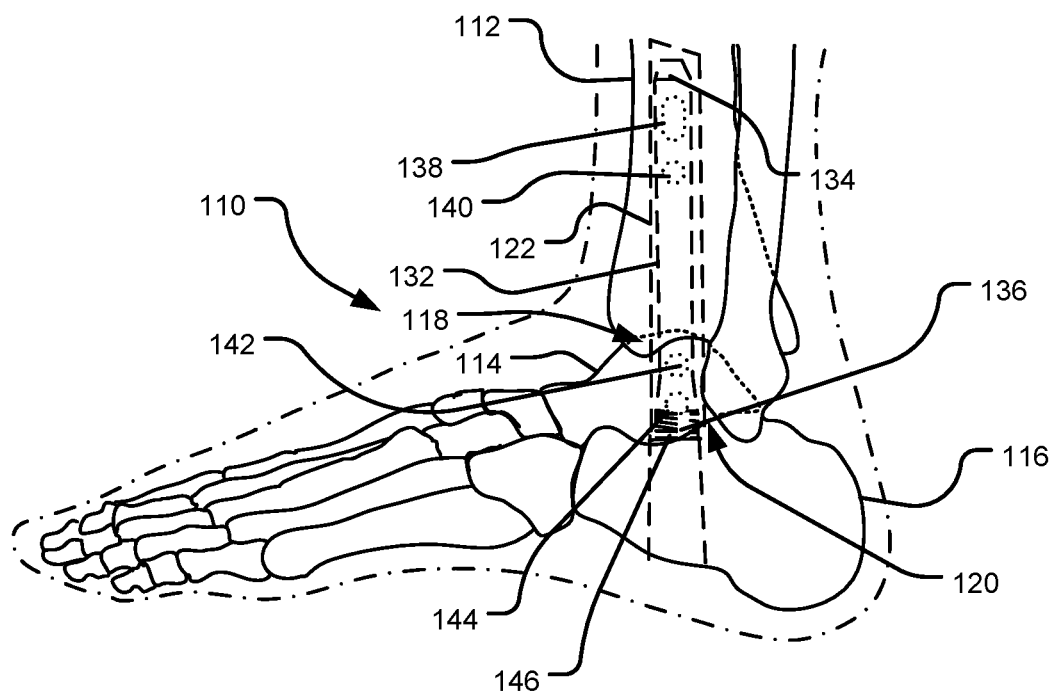
FIG. 14 illustrates an example of an intramedullary nail of the present disclosure in an inserted position with an end cap in a distal portion of the intramedullary nail.

The fixture 150 may include guides for insertion of locking fasteners to engage the intramedullary nail 130 such as discussed in greater detail below in relation to FIGS. 12 and 16-18. Subsequent to the placement of the intramedullary nail 130 and insertion of the appropriate locking fasteners, the fixture 150 may be disengaged from the distal end portion 136 of the intramedullary nail 130 for retraction of the fixture 150 from the bore 122. Furthermore, as shown in FIG. 14, an end cap 146 may be provided in a distal end portion 136 of the intramedullary nail 130. This may limit ingress of tissue into the distal end portion 136 of the intramedullary nail 130.

In one example, the distal end portion 136 of intramedullary nail 130 may include a threaded interface that is engaged by corresponding threads of the proximal portion of the fixture 150. In this regard, the fixture 150 may threadingly engage the intramedullary nail 130 for selective engagement and disengagement therewith. In any regard, the fixture 150 may be disengaged from the distal end portion 136 of the intramedullary nail 130 for retraction of the fixture 150 from a portion of the bore 122 extending through the calcaneus 116, thus leaving the intramedullary nail 130 in position proximal to the subtalar joint 120. Furthermore, the end cap 146 may also be threaded to threadingly engage the intramedullary nail 130 upon retraction of the fixture 150 as shown in FIG. 14.

The intramedullary nail 130 may be secured in position such that the distal end portion 136 is disposed proximal to the subtalar joint 120. In this regard, once the fixture 150 has been removed from the bore 122, the subtalar joint 120 may be free from obstruction. Accordingly, the intramedullary nail 130 may targeted arthrodesis of the tibiotalar joint 118. As the only impact to the subtalar joint 120 may be the creation of the bore 122, the subtalar joint 120 may be unaffected such that articulation of the subtalar joint is preserved upon arthrodesis of the tibiotalar joint 118.

Figure 5:
FIG. 5 illustrates an example of a portion of articular surface of the subtalar joint disrupted when creating a bore for insertion of an intramedullary nail of the present disclosure.

With respect to disruption of the subtalar joint 120, it has been recognized in the present disclosure that creation of a bore for insertion of an intramedullary nail 130 may have minimal impact on the subtalar joint 120. To support this, a number of cadaver studies were conducted, the results of which are generally represented in FIG. 5. Cadaveric specimens 500 were obtained. The tibiotalar joint was disarticulated on each cadaveric specimen 500 to expose the superior aspect of the talus 502. Subsequently, a guide wire was drilled from the central dome of the talus 502 through the calcaneus 504. An 11 mm reamer was then passed over the guide wire to create a bore 506 through the talus 502 and calcaneus 504 to simulate retrograde reaming to create the bore 506 for accepting an intramedullary nail. Subsequent to bore creation, the subtalar joint 508 was dissected open and the articular surface 510 was documented as shown in FIG. 5. FIG. 5 illustrates an example of the dissected subtalar joint 508 with the inferior aspect of the talus 502 illustrated on the left and the superior aspect of the calcaneus 504 on the right. The articular surfaces 510 of the talus 502 and the calcaneus 504 were measured, as represented by the cross hatched portion in FIG. 5. In addition, measurement of the disrupted articular surfaces 512 of the talus 502 and calcaneus 504 were also measured as represented by the shaded portion in FIG. 5. Specifically, measurements were conducted using software that calculated two-dimensional surface area to determine the percentage of actual subtalar joint area that was affected by the creation of the bore 506. The mean percentage of disrupted articular area 512 of the articular surface 510 that was removed with the reamer was then calculated.

Among the specimens, in the calcaneus, the mean total articular surface area 510 was 599 mm$^2$±113 mm$^2$ and the mean disrupted articular area 512 was 21 mm$^2$±16 mm$^2$. The percentage of the calcaneal articular surface that was removed during bore creation was 3.4%±1.9%. In the talus, the mean total articular area was 782 mm$^2$±130 mm$^2$ and the mean drilled articular area was 39 mm$^2$±18 mm$^2$. The percentage of the talar articular surface that was removed with the reamer was 5.0%±2.3%. Additionally, given an 11 mm reamer makes a circular surface area of 95 mm$^2$, the statistics above indicate that a significant portion of the reamed area is nonarticular, within the calcaneal sulcus or the talar sulcus.

Accordingly, only about 3.4% of the calcaneal articular surface and about 5% of the talar articular surface are affected in bore creation. Therefore, the majority of the articular surface 510 is left intact, which is ideal in optimizing the subtalar joint when performing targeted arthrodesis of the tibiotalar joint.

Figure 3:
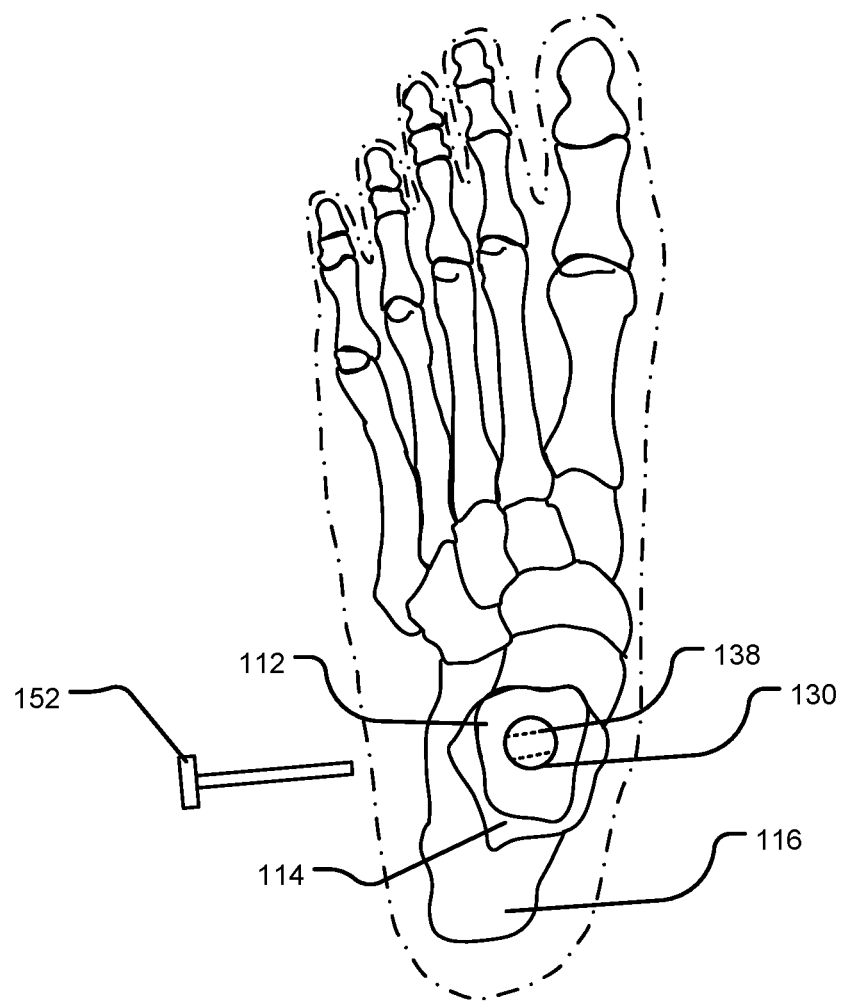
FIG. 3 includes a top view of an example of an intramedullary nail of the present disclosure with a tibia locking fastener in position for insertion.
Figure 4:
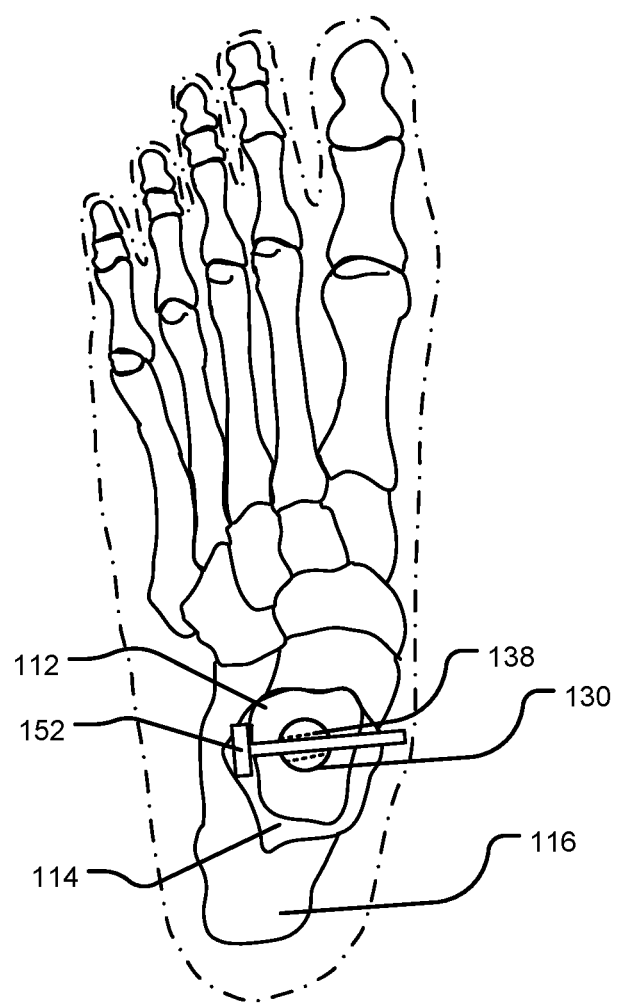
FIG. 4 includes a top view of an example of an intramedullary nail of the present disclosure with a tibia locking fastener inserted to secure the intramedullary nail with respect to the tibia.

With further reference to FIG. 3, a top view of the ankle anatomy of a patient 110 is shown. Once the intramedullary nail 130 is disposed in the tibia 112, a tibia locking fastener 152 may be positioned for insertion. While not shown in FIG. 3, the fixture 150 shown in FIG. 2 may include guides adapted to position the tibia locking fastener 152 in relative position to the intramedullary nail 130 (e.g., to align the tibia locking fastener 152 with a corresponding proximal aperture of the intramedullary nail 130). Of particular note, the tibia locking fastener 152 may be adapted for insertion into the tibia laterally through the proximal aperture 138 of the intramedullary nail 130. That is, the tibia locking fastener 152 may be introduced in a lateral-to-medial direction to provide ease of insertion without requiring the patient to be repositioned from a supine position or without requiring manipulation of the contralateral leg. With further reference to FIG. 4, the tibia locking fastener 152 may be inserted into the tibia for bicortical engagement to secure the intramedullary nail 130 with respect to the tibia 112. While not shown in FIGS. 3 and 4, more than one tibia locking fastener 152 may be utilized, each of which may engage a corresponding proximal aperture 138 of the intramedullary nail 130. The tibia locking fastener 152 may comprise any appropriate surgical fastener including a bolt, screw, wire, or other fastener hardware without limitation.

Figure 6:
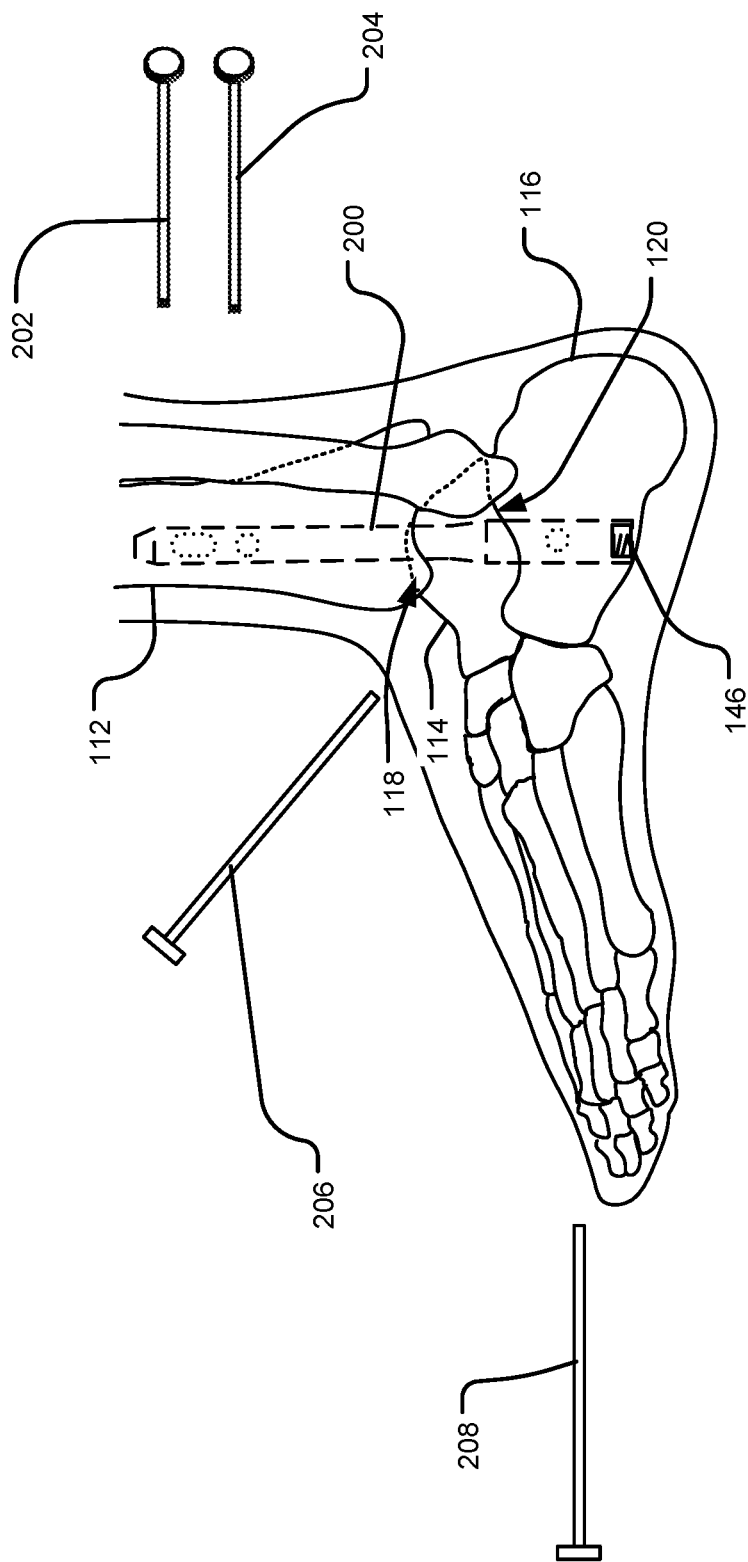
FIG. 6 includes a side view an example of an intramedullary nail of the present disclosure for tibiotalocalcaneal arthrodesis with locking fasteners in aligned position prior to insertion.
Figure 7:
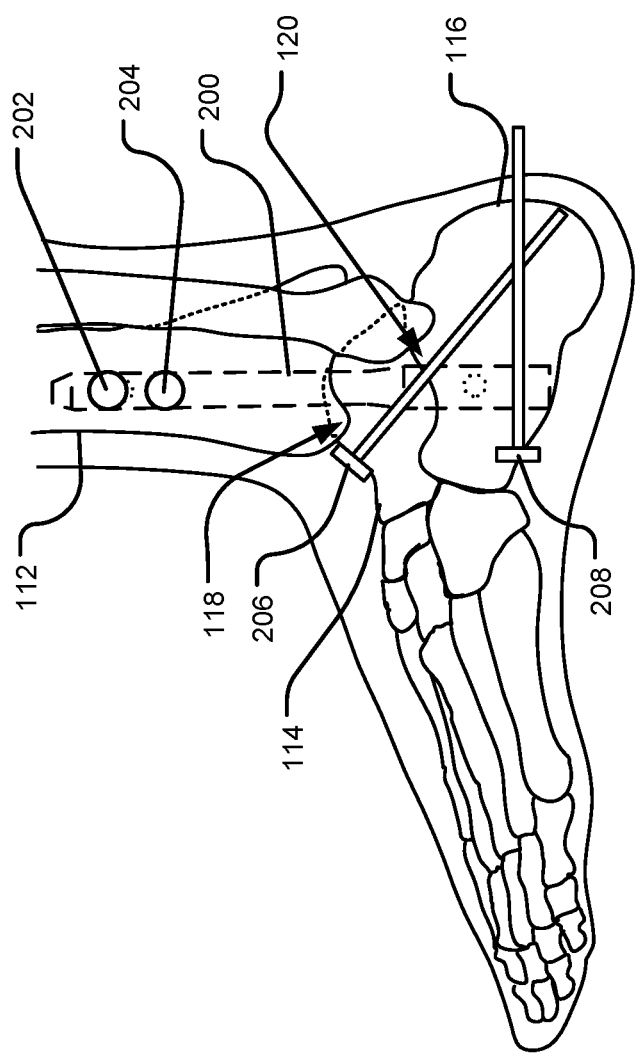
FIG. 7 includes a side view of an example of an intramedullary nail of the present disclosure for tibiotalocalcaneal arthrodesis with locking fasteners inserted to secure the intramedullary nail in position FIG. 8 includes a top view an example of an intramedullary nail of the present disclosure for tibiotalocalcaneal arthrodesis with locking fasteners in aligned position prior to insertion.
Figure 8:
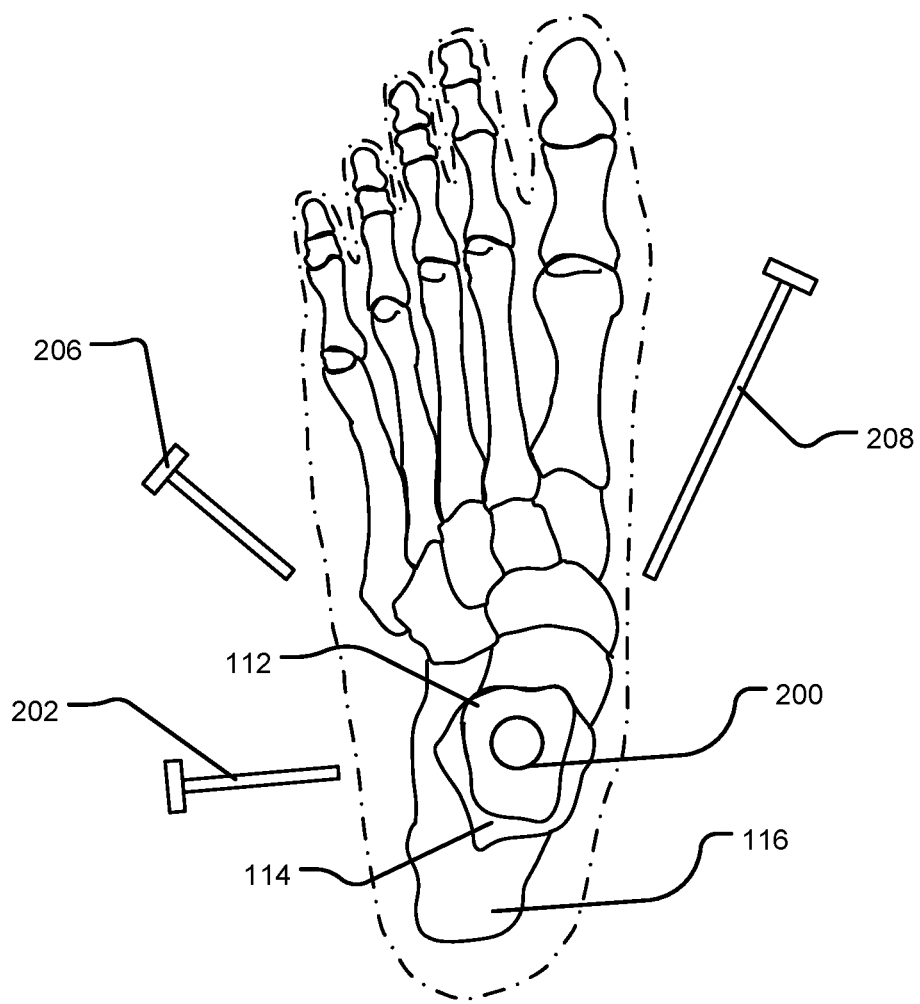
Figure 9:
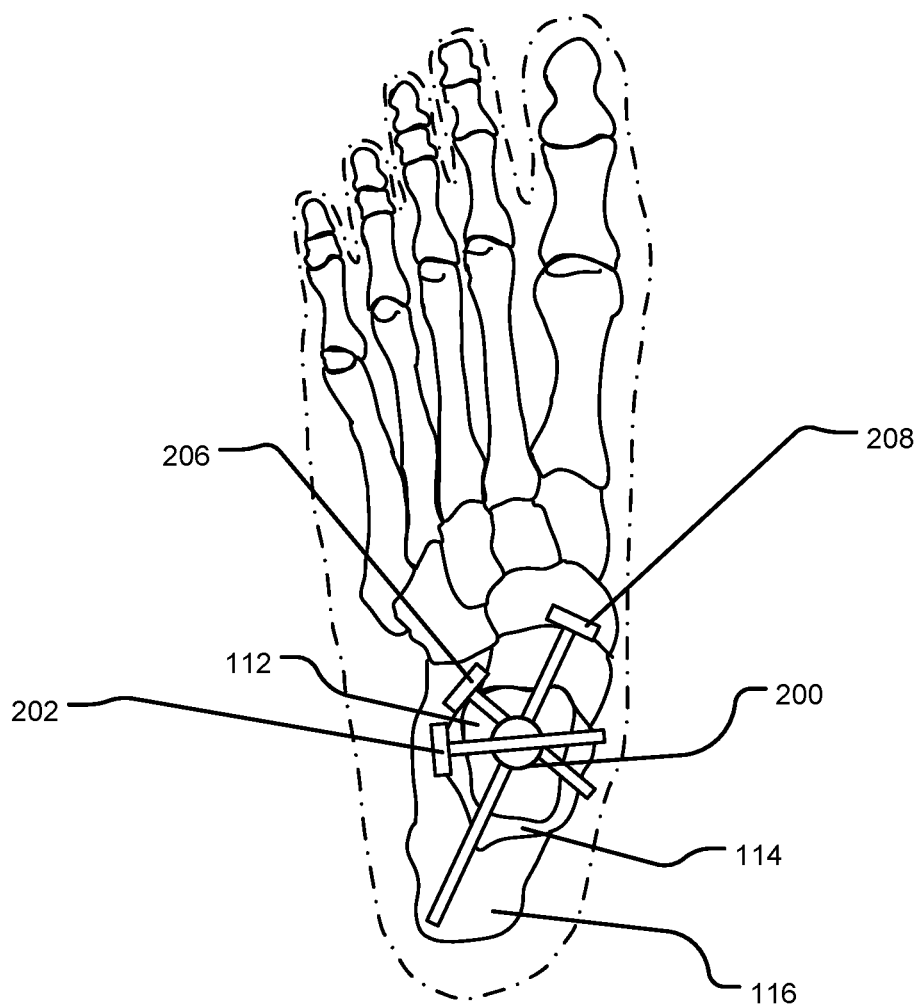
FIG. 9 includes a top view of an example of an intramedullary nail of the present disclosure for tibiotalocalcaneal arthrodesis with locking fasteners inserted to secure the intramedullary nail in position

FIG. 6 illustrates an alternative example of an intramedullary nail 200. The intramedullary nail 200 may comprise a tibiotalocalcaneal (TTC) nail that may be positioned within the tibia 112, talus 114, and calcaneus 116 to provide arthrodesis of the tibiotalar joint 118 and the subtalar joint 120. In the example illustrated in FIG. 6, a first tibia locking fastener 202 and a second tibia locking fastener 204 are shown in a retracted position for lateral-to-medial insertion. That is, the first tibia locking fastener 202 and the second tibia locking fastener 204 may be advanced laterally to secure the intramedullary nail 200 with respect to the tibia 112. Furthermore, a talus locking fastener 206 is illustrated in a retracted position for anterior or anterior-lateral introduction of the talus locking fastener 206. The talus locking fastener 206 may be inserted into the talus 114 to engage the intramedullary nail 200 (e.g., by passing through a distal aperture of the intramedullary nail 200). Furthermore, a calcaneus locking fastener 208 may be provided to secure the intramedullary nail 200 relative to the calcaneus 116. The calcaneus locking fastener 208 may also be position for lateral or anterior/lateral insertion. Thus, as shown in FIG. 7, the intramedullary nail 200 may be secured through the laterally advanced tibia locking fasteners 202 and 204, the laterally advanced talus locking fastener 206, and the laterally advanced calcaneus locking fastener 208. FIG. 8 provides a top view of the tibia locking fastener 202, talus locking fastener 206, and the calcaneus locking fastener 208 in a disengage position where the fasteners are aligned for insertion. FIG. 9 shows a top view of the fasteners in an inserted position.

Figure 15:
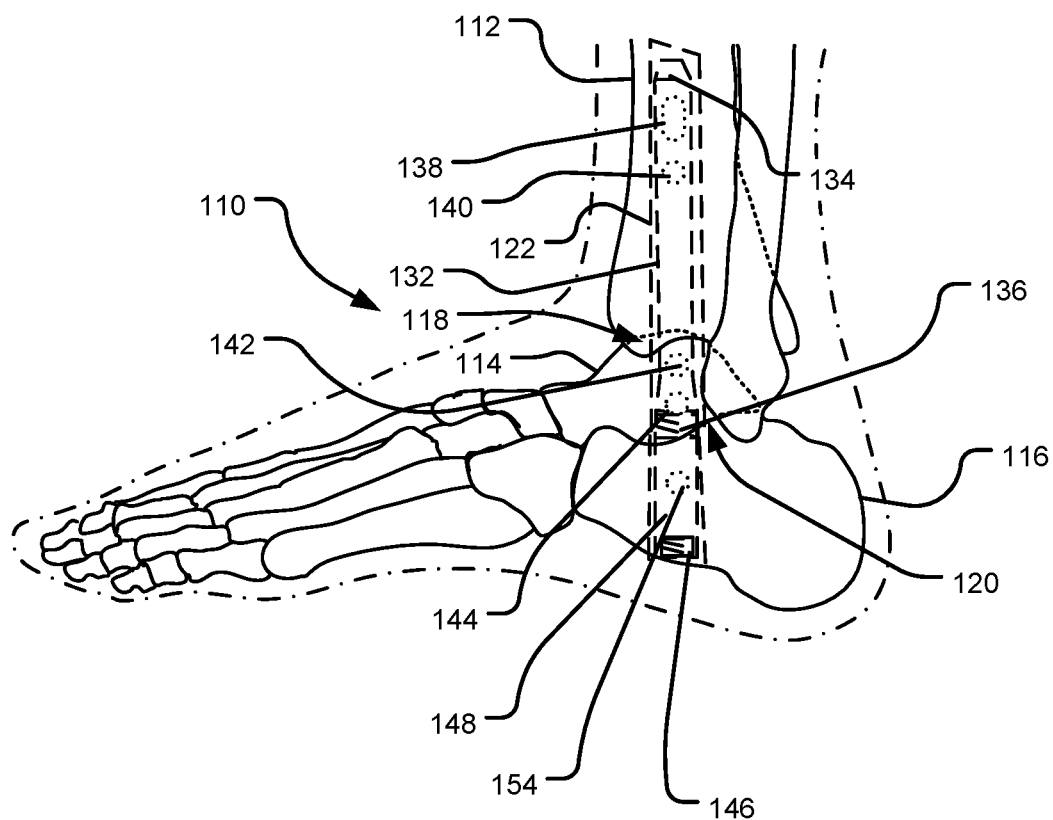
FIG. 15 illustrates an example of an intramedullary nail of the present disclosure including a tibiotalocalcaneal arthrodesis extension.

Further still, FIG. 15 illustrates another example in which the intramedullary nail 130 may be extended from a tibiotalar arthrodesis to a tibiotalocalcaneal arthrodesis. Specifically, in FIG. 15, an end cap 146 may be removed from the intramedullary nail 130 (e.g., in a revision procedure or as a further step in original placement of the intramedullary nail 130). In turn, a tibiotalocalcaneal arthrodesis extension 148 may be engaged with the distal end portion 136 of the intramedullary nail 130. Continuing the example, above, the tibiotalocalcaneal arthrodesis extension 148 may be threadingly engaged with the distal end portion 136 of the intramedullary nail 130. In this regard, the intramedullary nail 130 may be extended for full tibiotalocalcaneal arthrodesis. As noted above, this may be provided in a revision procedure. In this regard, it may be appreciated that the same approach through the bore 122 may be used to advance the tibiotalocalcaneal arthrodesis extension 148 into engagement with the distal end portion 136 of the intramedullary nail 130. Furthermore, the tibiotalocalcaneal arthrodesis extension 148 may include an aperture 154 to secure the tibiotalocalcaneal arthrodesis extension 148 with respect to the calcaneus 116. The fixture 150 may be used to apply compression across the subtalar joint 120 such as through use of an internally threaded bore and compression screws as described in greater detail below. As shown, an end cap 146 may be secured to a distal portion of the tibiotalocalcaneal arthrodesis extension 148.

Figure 10:
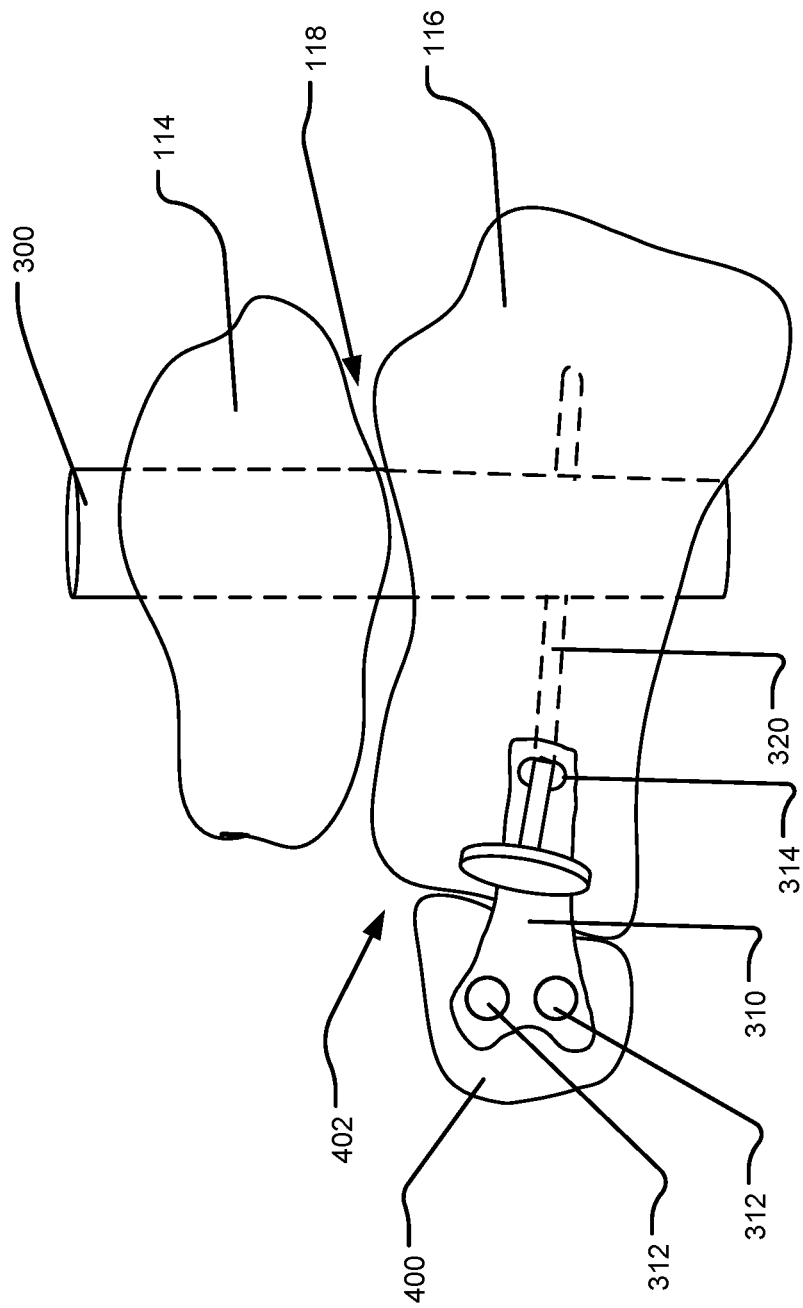
FIG. 10 illustrates an example of use of a plate with an intramedullary nail of the present disclosure for extended arthrodesis of the calcaneocuboid joint.

In addition to providing tibiotalar joint arthrodesis or full ankle arthrodesis of tibiotalar and subtalar joints, FIG. 10 illustrates another example in which an extension plate 310 may be utilized in conjunction with any of the foregoing embodiments to provide pantalar arthrodesis. Specifically, in FIG. 10, the extension plate 310 may be secured by a locking fastener 320 that is inserted into the calcaneus 116 to secure an intramedullary nail 300 with respect thereto. That is, the extension plate 310 may be captured by the locking fastener 320 by passing through an opening 314 of the extension plate 310 positioned adjacent to the calcaneus 116. In turn, the extension plate 310 may extend across the calcaneocuboid joint 402. In turn, one or more plate fasteners 312 may extend through the extension plate 310 and engage the cuboid 400. Thus, the extension plate 310 may be affixed to the cuboid 400 and calcaneus 116, respectively, to provide arthrodesis of the calcaneocuboid joint 402 in conjunction with arthrodesis of the tibiotalar joint 118 as described above.

Figure 11:
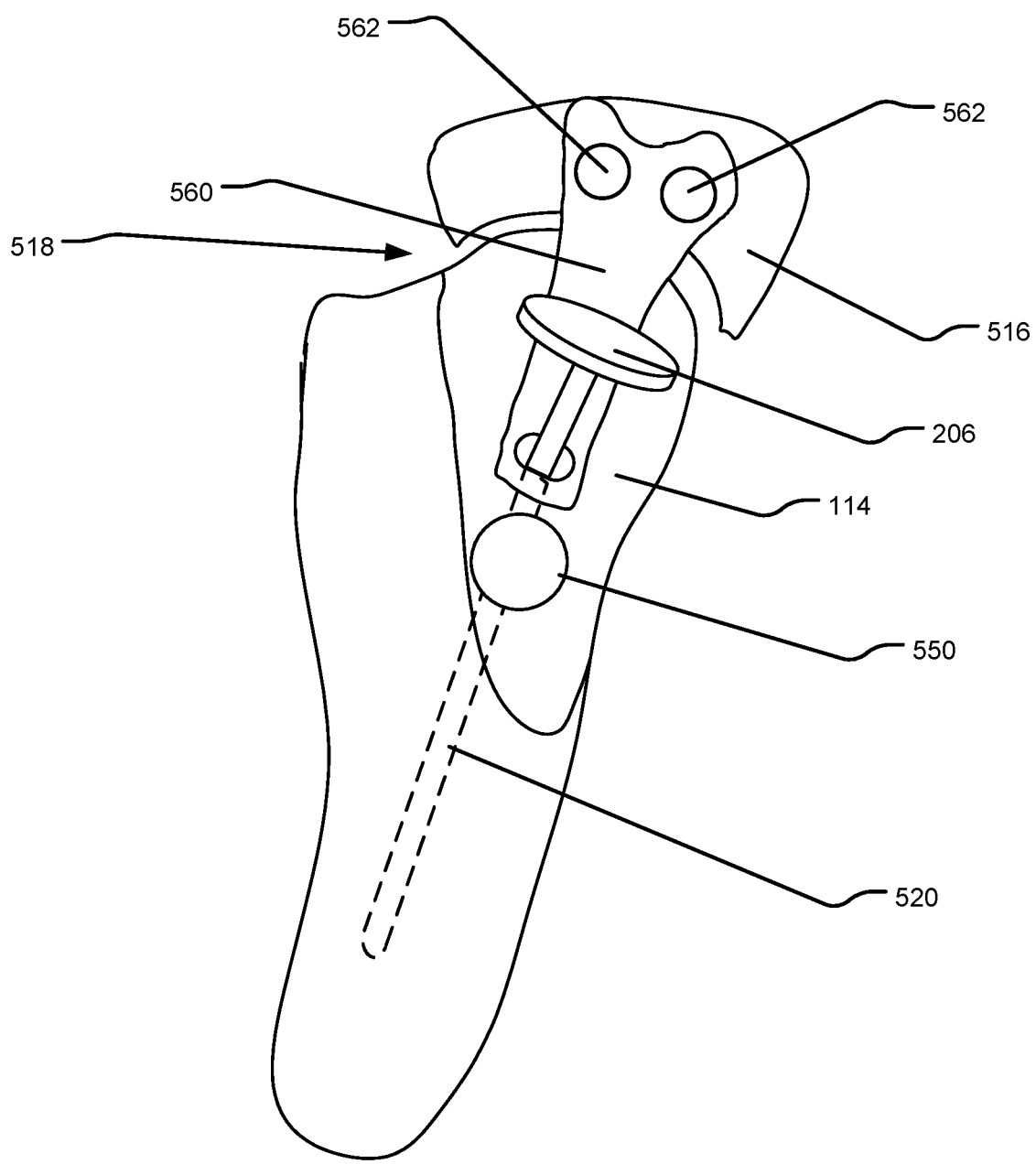
FIG. 11 illustrates an example of use of a plate with an intramedullary nail of the present disclosure for extended arthrodesis of the talonavicular joint.

FIG. 11 illustrates another example in which an extension plate 560 may be secured with a talus locking fastener 520 to the talus 114. In turn, the talus locking fastener 520 may engage an intramedullary nail 550 provided for arthrodesis of the tibiotalar joint and/or the subtalar joint. The extension plate 560 may extend across the talonavicular joint 518 such that one or more navicular fasteners 562 engage the navicular bone 516 to secure the extension plate 560 with respect thereto. In this regard, one or more of the examples shown in FIG. 10 or FIG. 11 may be provided for pantalar arthrodesis in conjunction with use of an intramedullary nail as described herein.

Figure 12:
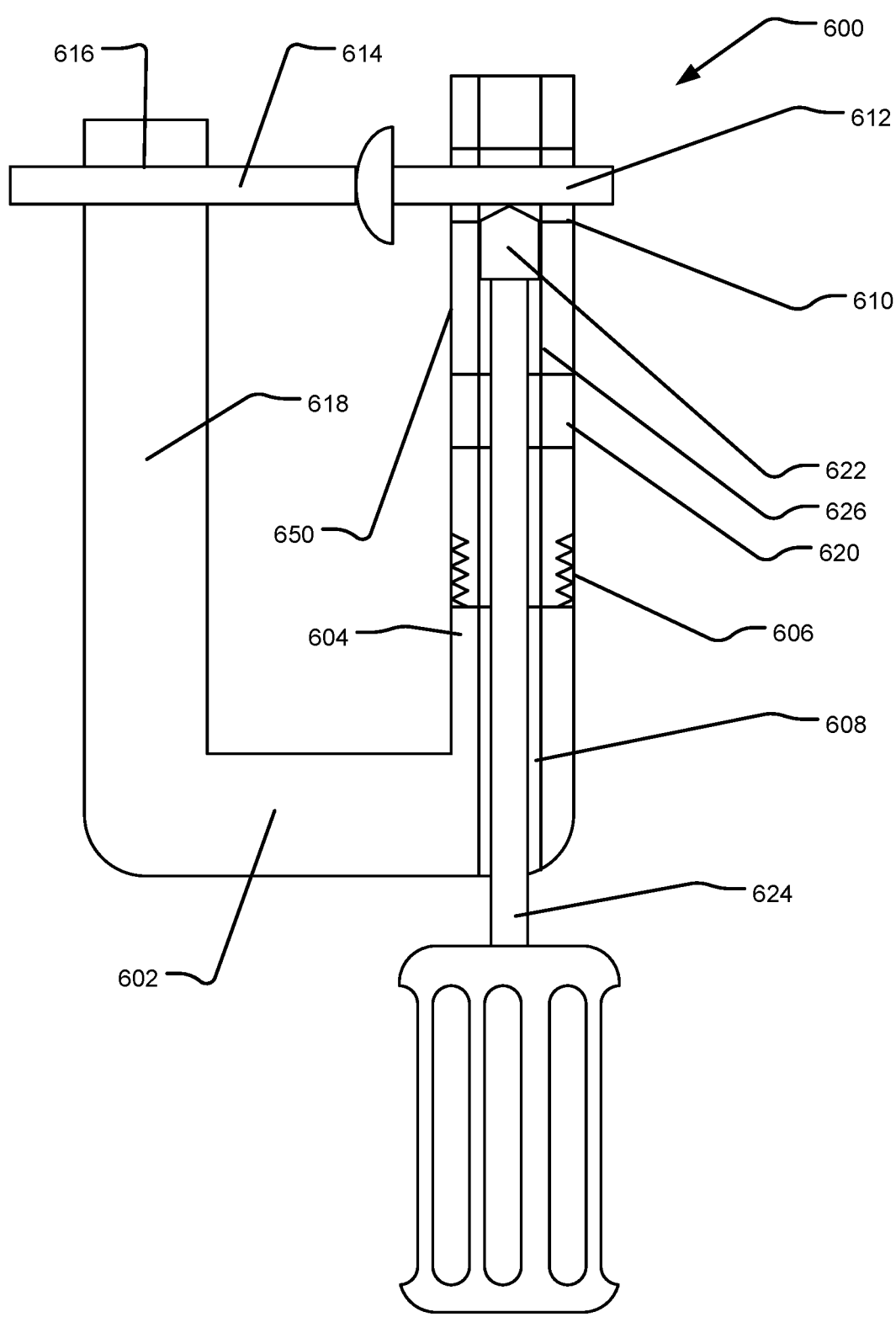
FIG. 12 illustrates an example of a jig for insertion of an intramedullary nail that includes one or more guides for locking fasteners that may be secured to impart a compressive force across a joint.

FIG. 12 illustrates an example of a fixture 600 that may be utilized in conjunction with placement of an intramedullary nail 650 according to the foregoing disclosure. The fixture 600 may comprise an engagement portion 604 that may engage with a distal end portion 606 of the intramedullary nail 650. For example, as described above, the engagement portion 604 and the distal end portion 606 of the intramedullary nail 650 may provide for selective engagement and disengagement of the fixture 600 with respect to the intramedullary nail 650. In one example, this interface may comprise a threaded interface to allow for selective engagement and disengagement between the fixture 600 and the intramedullary nail 650.

The fixture 600 may include a lateral extension 602 and a fastener guide 618 that extends with respect thereto. The fastener guide 618 may include a sleeve 616 through which a tool 614 may be advanced to guide placement of a locking fastener 612 with respect to an aperture 610 of the intramedullary nail 650. In addition, the fixture 600 may include a channel 608. The channel 608 may provide continuity to an inner cannula 626 of the intramedullary nail 650. In this regard, a set screw 622 may be advanced through the channel 608 and inner cannula 626 such the set screw 622 is positioned relative to the aperture 610 for engagement of the locking fastener 612. In addition, the channel 608 and inner cannula 626 may accept a tool 624 that may engage the set screw 622 to advance the set screw 622 into locking engagement with the locking fastener 612. For example, the inner cannula 626 may include a threaded portion corresponding to threads on the set screw 622 to facilitate advancement of the set screw 622 within the inner cannula 626 (e.g., by turning the set screw 622 using the tool 624).

In addition, advancing the set screw 622 with respect to the locking fastener 612 may facilitate application of a dynamic compressive force (e.g., in conjunction with a proximal locking fastener disposed in an elongated proximal aperture not shown in FIG. 12). In addition, at least one other aperture 620 provided in the intramedullary nail 650 may also accept a locking fastener (not shown in FIG. 12). In this regard, the other locking fastener not shown in FIG. 12 may similarly be engaged with a set screw that is advanced through the inner cannula 626 and channel 608.

Figure 13:
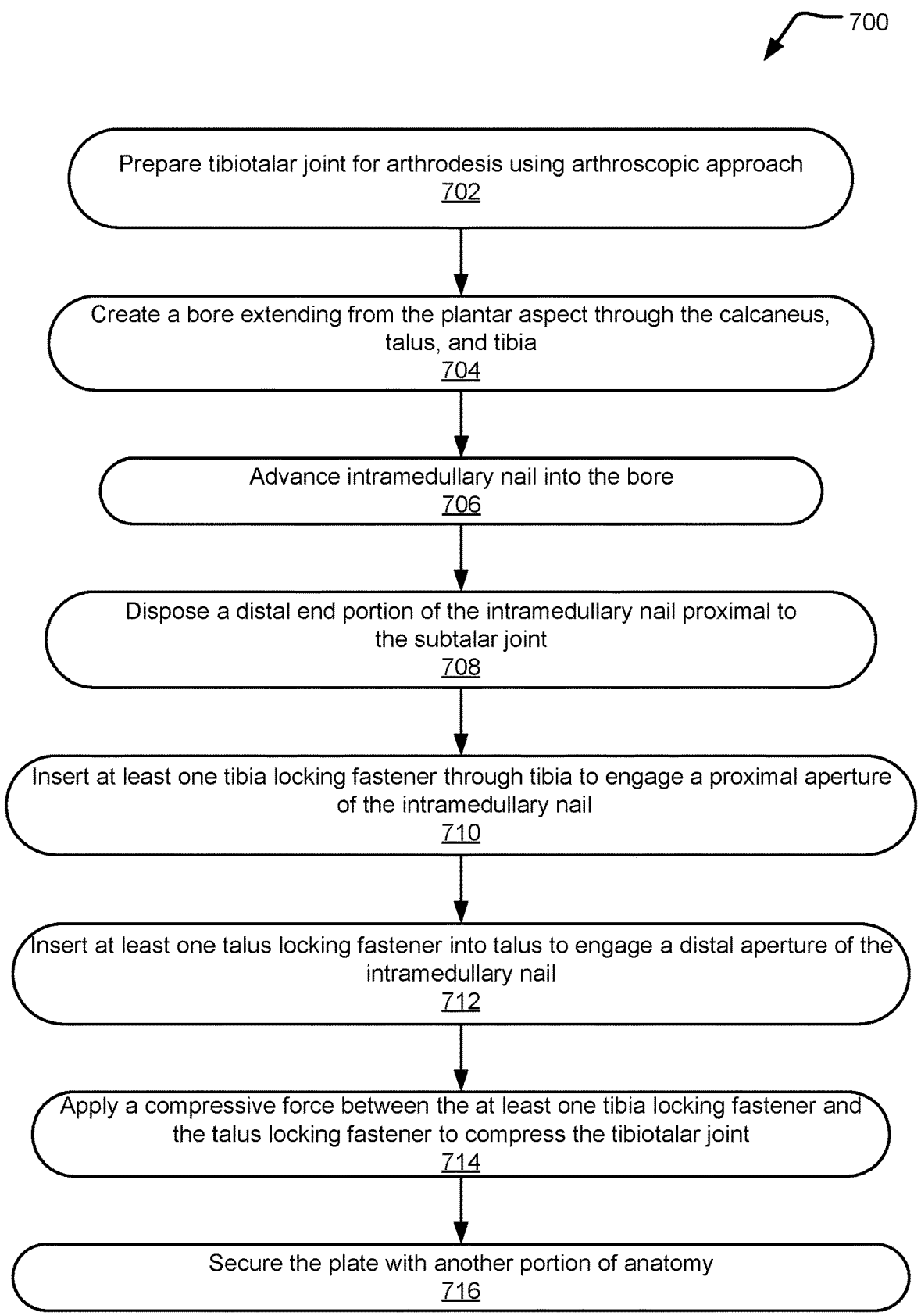
FIG. 13 includes example operations of a method of the present disclosure.

FIG. 13 illustrates example operations 700 according to the presence closure. The operations 700 may include a preparation operation 702 in which the tibiotalar joint may be prepared for arthrodesis. Specifically, the preparation operation 702 may include use of an arthroscopic approach for preparation of the tibiotalar joint. The operations 700 may also include a boring operation 704 in which a bore is created that extends from a plantar aspect through the calcaneus, talus, and tibia. As described above, the boring operation 704 may include initial placement of a guidewire into the desired anatomy to provide guidance of one or more reamers that may be introduced with respect to the guidewire to progressively create a bore of an appropriate size to accept an intramedullary nail.

In turn, an advancing operation 706 may be performed in which the intramedullary nail is advanced into the bore created through the calcaneus, talus, and tibia. A positioning operation 708 may be performed in which a distal end portion of the intramedullary nail is disposed proximal to the subtalar joint. In this regard, targeted arthrodesis of the tibiotalar joint may be achieved while providing minimal disruption to the subtalar joint. That is, the intramedullary nail may not extend across the subtalar joint as the positioning operation 708 may dispose the intramedullary nail proximal to the subtalar joint to allow for continued articulation of the subtalar joint after placement of the intramedullary nail in the positioning operation 708.

An insertion operation 710 may be provided in which at least one tibia locking fastener may be inserted through the tibia to engage a proximal aperture of the intramedullary nail having been placed in the positioning operation 708. The tibia locking fastener may provide bicortical engagement of the tibia to secure the intramedullary nail relative to the tibia. While at least one tibia locking fasteners is described in the insertion operation 710, it may be appreciated a plurality of tibia locking fasteners may engage a corresponding plurality of proximal apertures of the intramedullary nail.

Another insertion operation 712 may also be performed in which at least one talus locking fastener may be engaged with the talus to engage a distal aperture of the intermedullary nail to secure the intramedullary nail relative to the talus. Accordingly, a compressing operation 714 may be performed in which a compressive force may be applied between the at least one tibia locking fastener and the talus locking fastener. In connection with the disclosure in FIG. 12, it may be appreciated that such compressive force may be achieved through application of a force to the talus locking fastener using a set screw advanced proximally through an inner cannula of the intramedullary nail. That is, upon advancement of the set screw with respect to the talus locking fastener, the talus locking fastener and tibia locking fastener may be urged together such that the tibiotalar joint is compressed between the tibia locking fastener and the talus locking fastener. Other means for achieving the compressive force may additionally or alternatively be applied such as through use of external fixation and/or clamps or other approaches to achieve the compressive force across the tibiotalar joint.

In addition, a securing operation 716 may be performed in which an extension plate may be secured as described in either FIG. 10 or FIG. 11 above. That is, an extension plate may be engaged by the at least one talus locking fastener. The extension plate may further be secured to another portion of anatomy to extend fixation to the another portion of anatomy. For example, with respect to the disclosures in FIG. 10 and FIG. 11, pantalar fusion may be achieved including arthrodesis of the talonavicular and/or calcaneocuboid joints through use of extension plates that are at least partially secured using a locking fastener that engages the intramedullary nail. That is, in the event that an extension plate is utilized, the plate may be secured during one of the insertion operations 710 or 712 such that the extension plate may be secured by one of the lock fasteners used to secure the intramedullary nail in place. The extension plate utilize may be selectively fastened to another portion of anatomy to be fixated to be fixed according to the particular requirements of the procedure.

Figure 16:
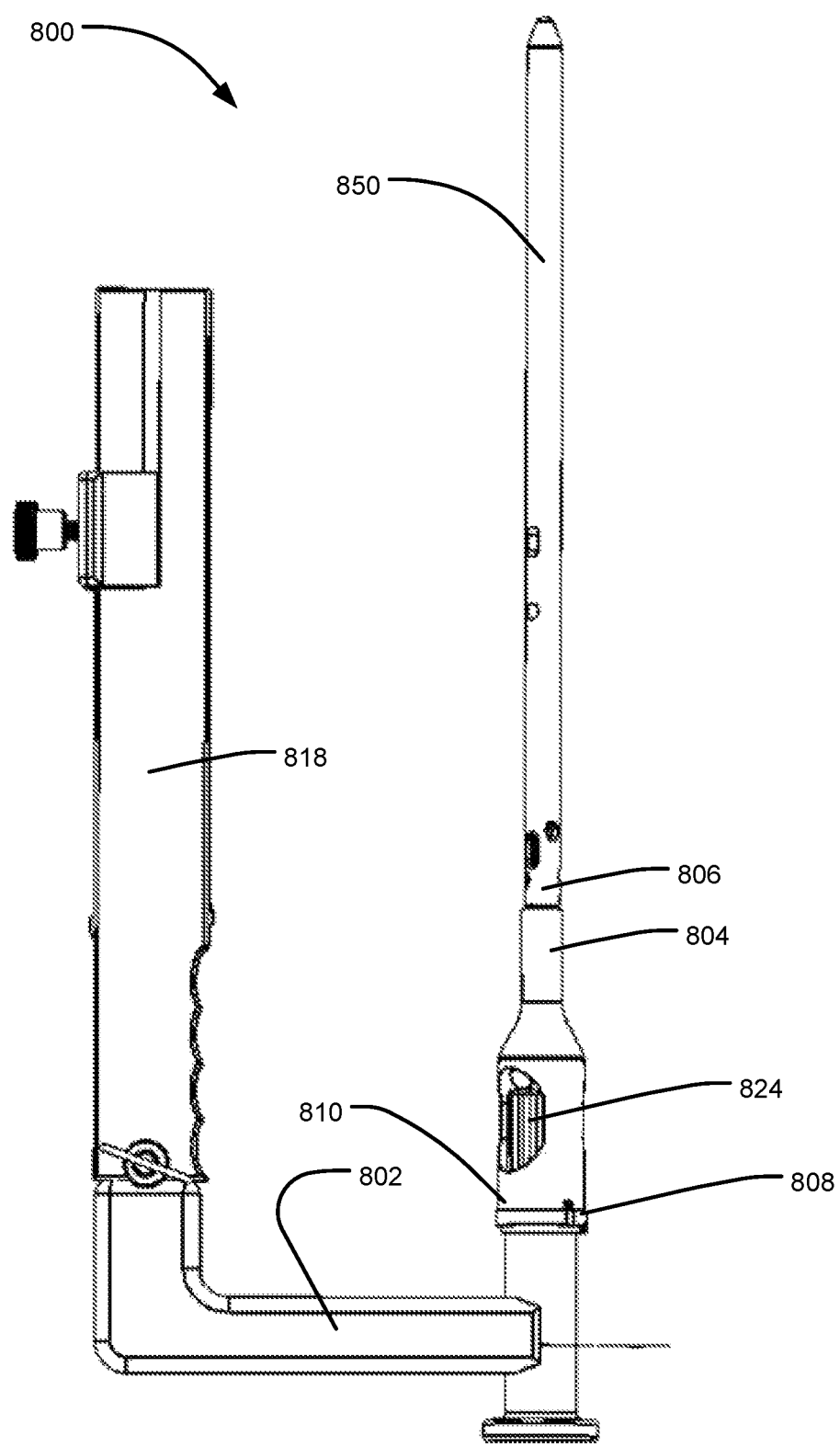
FIG. 16 illustrates another example of a jig for insertion of an intramedullary nail.
Figure 17:
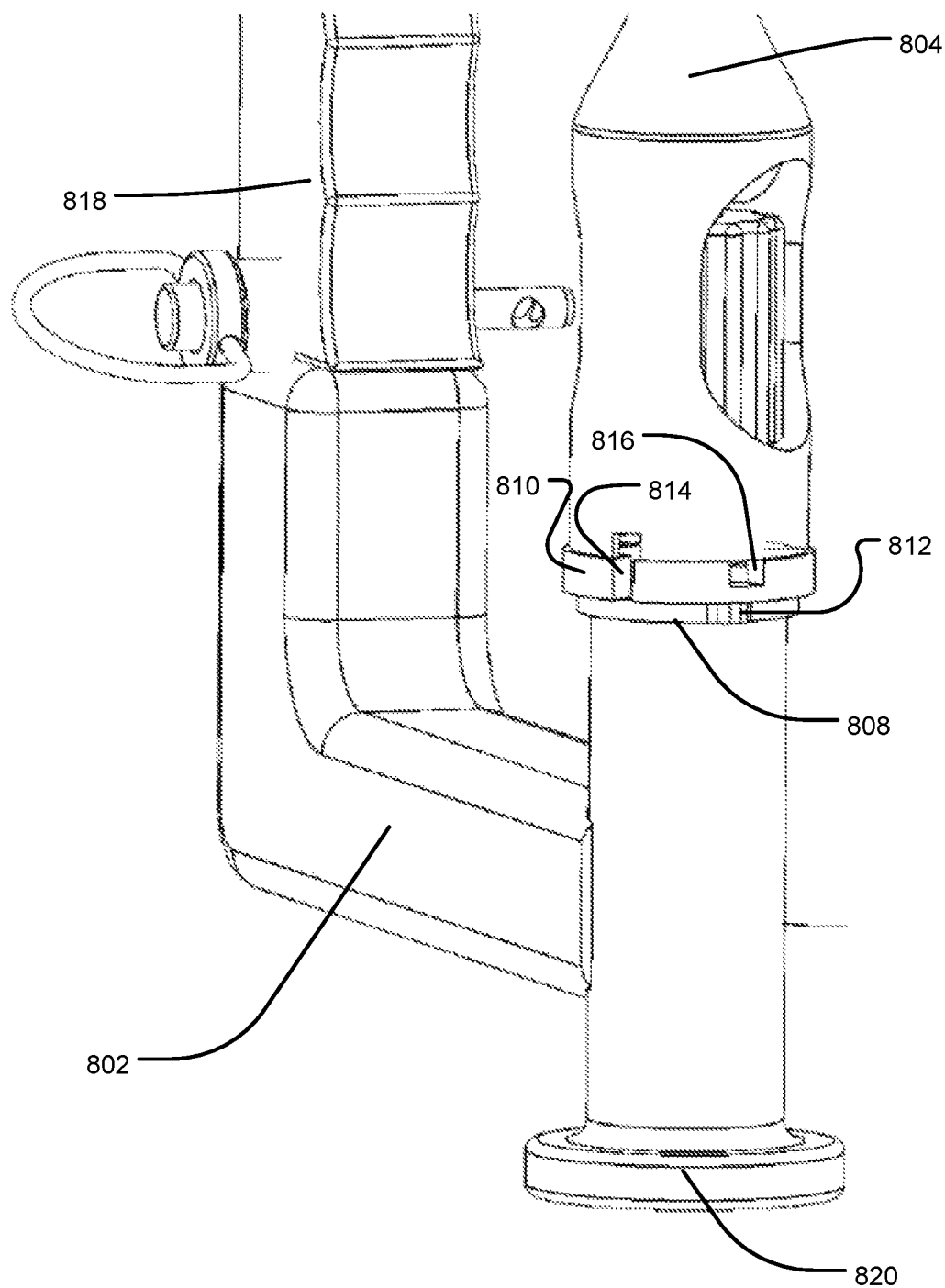
FIG. 17 illustrates a detailed view of an example of a jig for insertion of an intramedullary nail with indexing features.
Figure 18:
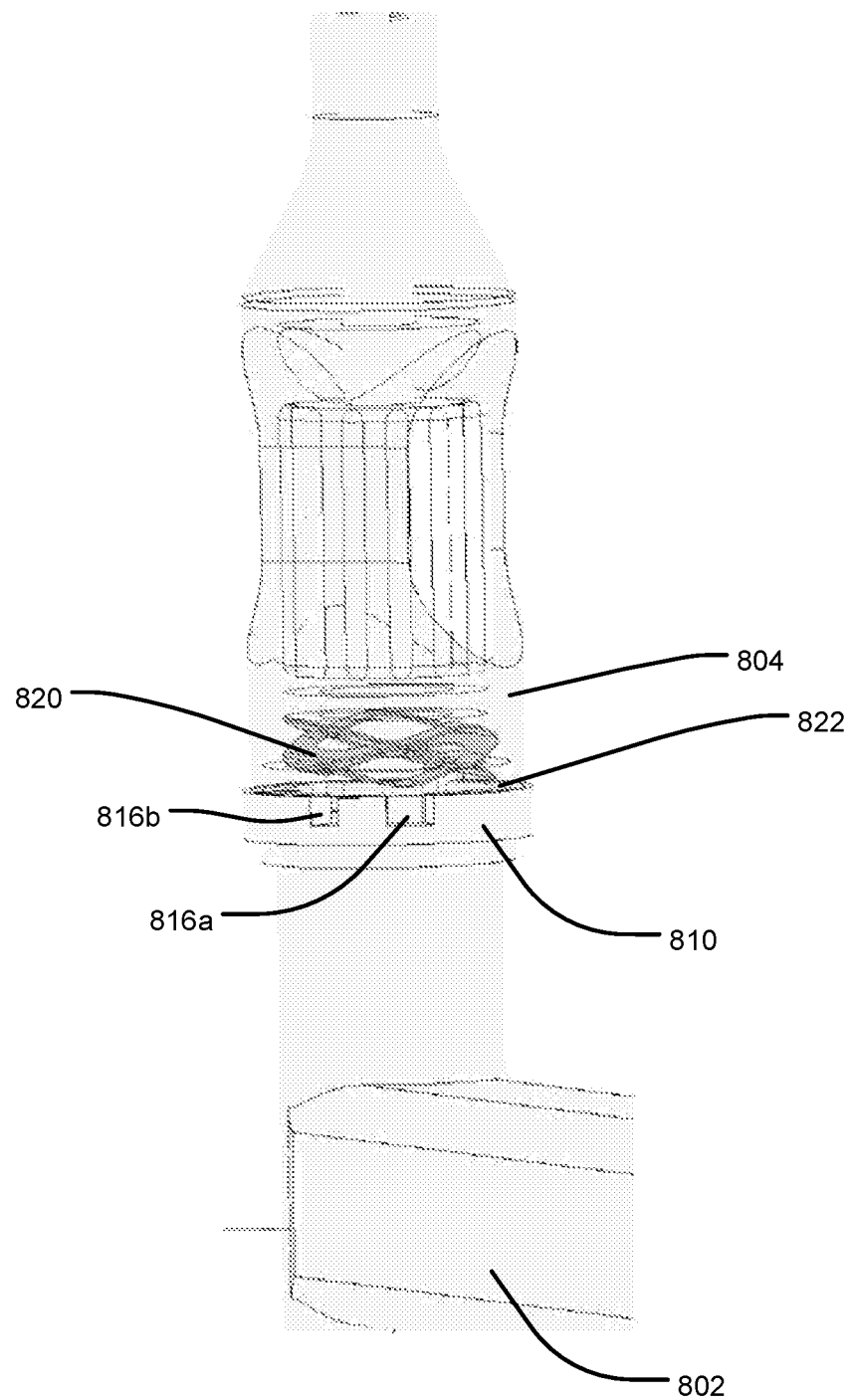
FIG. 18 illustrates a partially transparent view of a jig for illustration of the indexing features of FIG. 17.

FIGS. 16-18 illustrate another example of a fixture 800. The fixture 800 may be generally provided in accordance with the features and description provided above regarding FIG. 12 and the fixture 600. That is, the fixture 800 may include an engagement portion 804 that selectively engages a distal end portion 806 of an intramedullary nail 850 (e.g., via a threaded engagement). The fixture 800 may also include a lateral extension 802 that spaces a fastener guide 818 from the intramedullary nail 850. As such, the fastener guide 818 may include apertures or other guidance features that allow fasteners to be advanced relative to the intramedullary nail 850 to secure the intramedullary nail 850 as described above, although specific illustration of those features is omitted in FIGS. 16-18. Also, the fixture 800 includes a tool 824, which in the fixture 800 may be partially captured by the engagement portion 804. In any regard, the tool 824 may be used to engage/disengage the fixture 800 from the intramedullary nail 850 and/or to place compression screws or set screws in an inner cannula of the intramedullary nail 850.

The fixture 800 may also allow the lateral extension 802, and in turn, the fastener guide 818 to be rotationally indexed relative to the intramedullary nail 850. Specifically, the lateral extension 802 may extend from a fixture hub 808. The fixture hub 808 may be engaged with a flange 810 of the engagement portion 804. With further reference to FIG. 17, the fixture hub 808 may include a tab 812 extending radially from the fixture hub 808. The tab 812 may be advanced through a slot 814 in the flange 810 to allow the fixture hub 808 to advance proximally relative to the flange 810. In this regard, the fixture hub 808 may be concentrically disposed relative to the 810 to allow for rotation of the fixture hub 808 relative to the flange 810.

The arrangement shown in FIGS. 16-18 may allow the fixture hub 808, lateral extension 802, and fastener guide 818 to be rotated relative to the flange 810 about a longitudinal axis (e.g., extending along the length of and centrally to the intramedullary nail 850) of the intramedullary nail 850. In turn, upon rotation of the fixture hub 808 and lateral extension 802 about the longitudinal axis of the intramedullary nail 850, the fastener guide 818 may be positioned at different radial positions relative to the intramedullary nail 850.

Furthermore, the flange 810 may include an indexing position 816 for reception of the tab 812 to rotationally lock the flange 810 and the fixture hub 808. The indexing position 816 may define a pocket in the flange 810 for receiving the tab 812. When the tab 812 is received in the indexing position 816, the fixture hub 808 may be rotationally fixed relative to the flange 810 to prevent rotation of the fixture hub 808 relative to the flange 810.

With further reference to FIG. 18, an alternative view of the flange 810 is illustrated in which the engagement portion 804 is shown as transparent to allow for visibility of a biasing member 820 within the engagement portion 804. The fixture hub 808 may engage the biasing member 820 such that the fixture hub 808 is biased distally relative to the engagement portion 804 by the biasing member 820. As such, the advancement of the tab 812 through the slot 814 may be resisted by the biasing member 820, although the biasing member 820 is not visible in FIG. 17. In any regard, once the tab 812 has been advanced against the biasing member 820 to located it proximally to the slot 814, the tab 812 may be biased against a proximal internal surface 822 of the flange 810. The tab 812 may therefore bear against the proximal internal surface 822 under the biasing force of the biasing member 820. When the tab 812 is not disposed in an indexing position 816, the fixture hub 808 may freely rotate relative to the flange 810 to allow the lateral extension 802 and fastener guide 818 to be positioned relative to the intramedullary nail 850. When the tab 812 is aligned with an indexing position 816 (note that a first indexing position 816a and a second indexing position 816b are shown in FIG. 18), the tab 812 may be biased into the indexing position 816 to rotationally lock the fixture hub 808 relative to the flange 810 as described above. By providing a first indexing position 816a and second indexing position 816b, a number of preset locations of the lateral extension 802 and fastener guide 818 relative to the intramedullary nail 850 may be defined to, for example, provide alignment of apertures in the intramedullary nail 850 at different locations. Upon proximal movement of the tab 812 to a proximal position out of the indexing position 816, the fixture hub 808 may again be rotated relative to the flange 810 to allow for repositioning of the fixture hub 808 such as to be disposed in another of the indexing position 816.

One aspect of the present disclosure includes a method for tibiotalar arthrodesis. The method includes creating a bore extending from a plantar surface of a calcaneus bone through the calcaneus bone, subtalar joint, talus bone, and tibiotalar joint and terminating in intramedullary space of a tibia bone of a patient. The method also includes advancing an intramedullary nail through the bore. The method includes disposing a distal end portion of the intramedullary nail proximal to the subtalar joint. The method also includes securing the intramedullary nail with at least one tibia locking fastener and at least one talus locking fastener, each of which passes though respective apertures of the intramedullary nail. The method further includes compressing the tibiotalar joint by applying a compressive force between the tibia locking fastener and the talus locking fastener, wherein the subtalar joint remains free to articulate.

Implementations may include one or more of the following features in any combination. For example, the securing may include inserting the at least one tibia locking fastener laterally with respect to the tibia bone to extend through a proximal aperture of the intramedullary nail for bicortical fixation at a proximal portion of the intramedullary nail. In another example, the securing comprises may include inserting the talus locking fastener anteriorly with respect to the talus bone to extend through a distal aperture of the intramedullary nail for unicortical fixation at a distal portion of the intramedullary nail.

In an example, the distal aperture may be an elongated distal aperture and the compressing may include engaging the at least one talus locking fastener with a set screw disposed in an internal bore of the intramedullary nail. The compressing may also include advancing a set screw proximally within the internal bore of the intramedullary nail and applying a dynamic compressive force across the tibiotalar joint between the tibia locking fastener and the talus locking fastener in response to the advancing to urge the talus locking proximally within the elongated distal aperture.

In an example, the method may include preparing the tibiotalar joint for arthrodesis via arthroscopic access to the tibiotalar joint.

In an example, the bore may affect a minimal portion of an articular surface of the subtalar joint. For example, the bore may affect not more than about 5% of an articular surface area of the subtalar joint.

In another example, fixation may be extended to another adjacent joint. For example, the method may also include securing a plate with the talus locking fastener. The plate may extend across at least one other joint different than the tibiotalar joint to allow for arthrodesis of the at least one other joint. In various examples, the at least one other joint may be one or more of the talonavicular joint or the calcaneocuboid joint.

Another aspect of the present disclosure includes an intramedullary nail for tibiotalar arthrodesis. The nail includes a proximal end portion of the intramedullary nail adapted for insertion into an intramedullary space of a tibia bone of a patient. The nail also includes a distal end portion of the intramedullary nail adapted to extend across a tibiotalar joint such that a terminal end of the distal end portion is disposed in a talus bone proximal to a subtalar joint for isolated positioning of the intramedullary nail across the tibiotalar joint. The nail includes a body extending between the proximal end portion and the distal end portion. The nail includes at least one proximal aperture extending through the body for receipt of at least one tibia locking fastener and at least one distal aperture extending through the body for receipt of at least one talus locking fastener.

Implementations may include one or more of the following features in any combination. For example, the distal end portion may include a fixture interface adapted to engage a guide fixture that extends through a bore defined through a calcaneus bone and the subtalar joint for placement of the intramedullary nail through the talus bone, and the tibiotalar joint. The bore may affect a minimal portion of an articular surface of the subtalar joint. Specifically, the bore affect not more than about 5% of a surface area of the articular surface of the subtalar joint.

In an example, at least one proximal aperture is adapted to receive the at least one tibia locking fastener laterally with respect to the tibia bone to extend through the proximal aperture of the intramedullary nail for bicortical fixation at the proximal end portion of the intramedullary nail. Also, the distal aperture may be adapted to receive one talus locking fastener anteriorly with respect to the talus bone to extend through the distal aperture of the intramedullary nail for unicortical fixation at a distal portion of the intramedullary nail.

In an example, the body of the intramedullary nail may include an internal bore extending axially to receive a set screw advanceable proximally in the internal bore to contact the tibia locking fastener for application of a dynamic compressive force across the tibiotalar joint between the tibia locking fastener and the talus locking fastener.

In an example, the distal aperture may include an elongated aperture to allow for relative movement between the tibia locking fastener and the intramedullary nail in response to the dynamic compressive force.

Another aspect of the present disclosure includes a system for tibiotalar arthrodesis. The system includes an intramedullary nail comprising a body extending between a proximal end portion adapted for insertion into an intramedullary space of a tibia bone of a patient and a distal end portion adapted to extend across a tibiotalar joint such that a terminal end of the distal end portion is disposed in a talus bone proximal to a subtalar joint for isolated positioning of the intramedullary nail across the tibiotalar joint. The system also includes a fixture adapted for engagement with the proximal end portion of the intramedullary nail. The fixture is disposed in a bore extending through the calcaneus bone through which the intramedullary nail is inserted to dispose the fixture across the subtalar joint when the intramedullary nail is positioned across the tibiotalar joint to dispose the terminal end in the talus proximal to the subtalar joint. The system also includes at least one tibia locking fastener advanceable laterally with respect to the tibia to dispose the at least one tibia locking fastener through a proximal aperture extending through the body and at least one talus locking fastener advanceable anteriorly with respect to the talus to dispose the at least one talus locking fastener through a distal aperture extending through the body.

Implementations may include one or more of the following features in any combination. For example, the bore may affect a minimal portion of an articular surface of the subtalar joint. Specifically, the bore may affect not more than about 5% of a surface area of the articular surface of the subtalar joint.

In an example, the body of the intramedullary nail comprises an internal bore extending axially to receive a set screw advanceable proximally in the internal bore to contact the tibia locking fastener for application of a dynamic compressive force across the tibiotalar joint between the tibia locking fastener and the talus locking fastener. In addition, the distal aperture may be an elongated aperture to allow for relative movement between the talus locking fastener and the intramedullary nail in response to the dynamic compressive force.

In an example, the system also includes a plate adapted for engagement by the talus locking fastener to secure the plate relative to the talus. The plate may across at least one other joint different than the tibiotalar joint to allow for arthrodesis of the at least one other joint. For example, the at least one other joint may include one or more of the talonavicular joint or the calcaneocuboid joint.

While this specification contains many specific implementation details, these should not be construed as limitations on the scope of any technologies or of what may be claimed, but rather as descriptions of features specific to particular implementations of the particular described technology. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel operations may be advantageous.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

A number of implementations of the described technology have been described. Nevertheless, it will be understood that various modifications can be made without departing from the spirit and scope of the recited claims.

What is claimed is:

1. A method for tibiotalar arthrodesis, comprising:
creating a bore extending from a plantar surface of a calcaneus bone through the calcaneus bone, subtalar joint, talus bone, and tibiotalar joint and terminating in intramedullary space of a tibia bone of a patient;
advancing an intramedullary nail into the bore through the calcaneus bone and the subtalar joint;
disposing the intramedullary nail in the tibiotalar joint, with a distal end portion of the intramedullary nail proximal to the subtalar joint;
securing the intramedullary nail to the tibia bone with a tibia locking fastener and to the talus bone with a talus locking fastener, each of which passes though respective apertures of the intramedullary nail;
compressing the tibiotalar joint by applying a compressive force between the tibia locking fastener and the talus locking fastener; and
securing a plate with the talus locking fastener, wherein the plate extends across at least one other joint different than the tibiotalar joint to allow for arthrodesis of the at least one other joint;
wherein the talus bone and the calcaneus bone, forming the subtalar joint, remain free to move relative to each other.

2. The method of claim 1, wherein the securing the intramedullary nail comprises:
inserting the tibia locking fastener laterally with respect to the tibia bone to extend through a proximal aperture of the intramedullary nail for bicortical fixation at a proximal portion of the intramedullary nail.

3. The method of claim 2, wherein the securing the intramedullary nail comprises:
inserting the talus locking fastener anteriorly with respect to the talus bone to extend through a distal aperture of the intramedullary nail for unicortical fixation at a distal portion of the intramedullary nail.

4. The method of claim 3, wherein the distal aperture comprises an elongated distal aperture and compressing comprises:
engaging the talus locking fastener with a set screw disposed in an internal bore of the intramedullary nail;
advancing a set screw proximally within the internal bore of the intramedullary nail; and
applying a compressive force across the tibiotalar joint between the tibia locking fastener and the talus locking fastener in response to the advancing to urge the talus locking fastener proximally within the elongated distal aperture.

5. The method of claim 1, further comprising:
preparing the tibiotalar joint for arthrodesis via arthroscopic access to the tibiotalar joint.

6. The method of claim 1, wherein the bore affects not more than 5% of an articular surface area of the subtalar joint.

7. The method of claim 1, wherein the at least one other joint comprises one or more of a talonavicular joint or a calcaneocuboid joint.

8. A method for tibiotalar arthrodesis, comprising:
creating a bore extending from a plantar surface of a calcaneus bone through the calcaneus bone, through a subtalar joint, through a talus bone, through a tibiotalar joint and terminating in intramedullary space of a tibia bone of a patient;
advancing an intramedullary nail having a proximal end portion and a distal end portion into the bore;
disposing the proximal end portion in the tibia bone and the distal end portion of the intramedullary nail in the talus bone proximal to the subtalar joint;
compressing the tibiotalar joint by applying a compressive force between the tibia bone and the talus bone;
securing the intramedullary nail to the tibia bone with a tibia locking fastener and to the talus bone with a talus locking fastener; and
securing a plate with the talus locking fastener, wherein the plate extends across at least one other joint different than the tibiotalar joint to allow for arthrodesis of the at least one other joint.

9. The method of claim 8, wherein disposing the distal end portion of the intramedullary nail proximal to the subtalar joint comprises:
disposing the distal end portion of the intramedullary nail in the talus bone.

10. The method of claim 8, wherein the securing the intramedullary nail comprises:
inserting the tibia locking fastener laterally with respect to the tibia bone for bicortical fixation at a proximal portion of the intramedullary nail.

11. The method of claim 8, wherein the securing the intramedullary nail comprises:
inserting the talus locking fastener anteriorly with respect to the talus bone for unicortical fixation at a distal portion of the intramedullary nail.

12. The method of claim 8, wherein each of the tibia locking fastener and the talus locking fastener passes though respective apertures of the intramedullary nail.

13. The method of claim 8, wherein the securing comprises:
inserting the tibia locking fastener laterally with respect to the tibia bone to extend through a proximal aperture of the intramedullary nail for bicortical fixation at a proximal portion of the intramedullary nail; and
inserting the talus locking fastener anteriorly with respect to the talus bone to extend through a distal aperture of the intramedullary nail for unicortical fixation at a distal portion of the intramedullary nail.

14. The method of claim 8, further comprising:
preparing the tibiotalar joint for arthrodesis via arthroscopic access to the tibiotalar joint.

15. The method of claim 8, wherein the bore affects not more than 5% of an articular surface area of the subtalar joint.

16. The method of claim 8, wherein the at least one other joint comprises one or more of a talonavicular joint or a calcaneocuboid joint.

17. A method for tibiotalar arthrodesis, comprising:
creating a bore extending from a plantar surface of a calcaneus bone through the calcaneus bone, subtalar joint, talus bone, and tibiotalar joint and terminating in intramedullary space of a tibia bone of a patient;
advancing an intramedullary nail into the bore;
disposing a distal end portion of the intramedullary nail proximal to the subtalar joint;
securing the intramedullary nail with a tibia locking fastener and a talus locking fastener, each of which passes though respective apertures of the intramedullary nail;

securing a plate with the talus locking fastener, wherein the plate extends across at least one other joint different than the tibiotalar joint to allow for arthrodesis of the at least one other joint; and compressing the tibiotalar joint by applying a compressive force between the tibia locking fastener and the talus locking fastener.

18. The method of claim 17, wherein the at least one other joint comprises one or more of a talonavicular joint or a calcaneocuboid joint.

19. The method of claim 17, wherein the securing the intramedullary nail comprises:

inserting the tibia locking fastener laterally with respect to the tibia bone.

20. The method of claim 17, wherein the securing the intramedullary nail comprises:

inserting the talus locking fastener anteriorly with respect to the talus bone.

\* \* \* \* \*